United States Patent
Solomon et al.

(10) Patent No.: US 7,713,547 B2
(45) Date of Patent: *May 11, 2010

(54) METHOD OF ADMINISTERING A PARTIAL DOSE OF A SEGMENTED PHARMACEUTICAL TABLET

(75) Inventors: Lawrence Solomon, Boca Raton, FL (US); Allan S. Kaplan, Boca Raton, FL (US)

(73) Assignee: Accu-Break Pharmaceuticals, Inc., Plantation, FL (US)

( * ) Notice: Subject to any disclaimer, the term of this patent is extended or adjusted under 35 U.S.C. 154(b) by 949 days.

This patent is subject to a terminal disclaimer.

(21) Appl. No.: 11/441,456

(22) Filed: May 25, 2006

(65) Prior Publication Data

US 2007/0031488 A1 Feb. 8, 2007

Related U.S. Application Data

(63) Continuation-in-part of application No. PCT/US2005/018639, filed on May 23, 2005, and a continuation-in-part of application No. PCT/US2005/018638, filed on May 23, 2005, and a continuation-in-part of application No. PCT/US2005/018633, filed on May 23, 2005.

(60) Provisional application No. 60/573,042, filed on May 21, 2004, provisional application No. 60/573,134, filed on May 21, 2004.

(51) Int. Cl.
*A61K 9/20* (2006.01)
*A61K 9/44* (2006.01)

(52) U.S. Cl. .................. 424/464; 424/400; D24/100; D24/103

(58) Field of Classification Search .................. None
See application file for complete search history.

(56) References Cited

U.S. PATENT DOCUMENTS

| | | | |
|---|---|---|---|
| 3,128,226 A | | 4/1964 | Rubin et al. |
| 4,215,104 A | * | 7/1980 | Ullman et al. .............. 424/467 |
| 4,590,183 A | * | 5/1986 | Bailey .......................... 514/163 |
| 5,158,728 A | * | 10/1992 | Sanderson et al. .......... 264/113 |
| 5,562,920 A | * | 10/1996 | Demmer et al. ............. 424/464 |
| 5,817,340 A | | 10/1998 | Roche et al. |
| 6,086,919 A | | 7/2000 | Bauer et al. |
| 6,183,778 B1 | | 2/2001 | Conte et al. |
| 6,294,200 B1 | | 9/2001 | Conte et al. |
| 6,309,668 B1 | | 10/2001 | Bastin et al. |
| 6,919,373 B1 | | 7/2005 | Lam et al. |
| 7,011,849 B2 | | 3/2006 | Storm et al. |
| 2002/0132850 A1 | | 9/2002 | Bartholomaus |
| 2005/0038039 A1 | | 2/2005 | Fanara et al. |
| 2006/0280794 A1 | | 12/2006 | Hamaguchi et al. |
| 2007/0031494 A1 | * | 2/2007 | Solomon et al. ............ 424/472 |

OTHER PUBLICATIONS

Rosen. Behaviour Change vol. 19, No. 4 2002 pp. 183-190.*
H.A. Lieberman and L. Lachman, Pharmaceutical Dosage Forms, vol. 1, pp. 217-223, Marcel Dekker, Inc., New York, New York.

* cited by examiner

*Primary Examiner*—Yvonne L Eyler
*Assistant Examiner*—Lori Mattison
(74) *Attorney, Agent, or Firm*—Ted Whitlock

(57) ABSTRACT

A drug-containing pharmaceutical tablet adapted for accurate breaking which has two or more segments with at least one segment containing a drug.

27 Claims, 12 Drawing Sheets

METHOD OF ADMINISTERING A PARTIAL DOSE OF A SEGMENTED PHARMACEUTICAL TABLET

CROSS-REFERENCE TO RELATED APPLICATIONS

This is a continuation-in-part of International Applications PCT/US2005/018633; PCT/US2005/018638, and PCT/US2005/018639 filed 23 May 2005, each of which designates the United States and claims the benefit of U.S. Provisional Applications, Ser. Nos. 60/573,042 and Ser. No. 60/573,134 filed May 21, 2004.

FIELD OF THE INVENTION

The invention involves a method of providing a partial dose of a layered pharmaceutical tablet comprising a layer containing a drug and a layer either lacking a drug or containing said drug as part of a different granulation, such as a less concentrated form.

BACKGROUND

The subject invention derives from the need to solve at least two related problems within the pharmaceutical industry: (1) inaccurate or inconsistent dose division upon breaking of a dosage form, and (2) inflexibility in adjusting the dose of only one active ingredient in a combination dosage form.

With regard to the first problem of inconsistent or inaccurate dose division, it is known that pharmaceutical tablets are commonly broken to modify the dose provided in a whole tablet. In the U.S., many "managed care" insurance organizations recommend or encourage patients to split or divide tablets, including unscored or irregularly-shaped tablets. These dosage adjustments, achieved through tablet breaking by patients, have been determined to be imprecise. No known solution to the problem has been provided.

Tablets are often produced with a score to aid breaking, but such tablet breaking is well-documented to suffer many problems whether or not scoring of the tablet is provided. Scored pharmaceutical tablets, layered or non-layered, fail to adequately address the problem because of uneven breaking, chipping, or crumbling that occurs upon breaking. Scores formed into a tablet have heretofore not exceeded 1 mm in depth.

In 1984, Stimpel, et al., found that tablet breaking was not accurate, even if performed by a sophisticated, dexterous person. M. Stimpel, et al., "Breaking Tablets in Half." The Lancet (1984):1299.

In a report by Peek et al., "elderly patients" aged 50-79 using, without specific instruction, mechanical tablet splitters to break scored tablets produced highly unsatisfactory division of the tablets. Peek, B. T., Al-Achi, A., Coombs, S. J. "Accuracy of Tablet Splitting by Elderly Patients," The Journal of the American Medical Association 288 No. 4 (2002): 139-145. Many drugs, such as warfarin, require dosage adjustments. Peek, et al. found warfarin 5 mg was, on average, split into 1.9 and 3.1 mg tablets. This potent anticoagulant has such a narrow therapeutic range that 2, 2.5, and 3 mg tablet doses are manufactured. Biron, et al., demonstrated that warfarin 10 mg also often split to less than 4.25 or greater than 5.75 mg. Biron, C., Liczner, P., Hansel, S., Schved, J. F., "Oral Anticoagulant Drugs: Do Not Cut Tablets in Quarters," Thromb. Haemost. 1201 (1999). In addition, a statistically significant loss of mass resulted from crumbling or chipping when breaking the warfarin tablets.

Rodenhuis, et al., observed that, in 1998, European regulatory authorities started a policy to discourage scoring of tablets. N. Rodenhuis et al., "The rationale of scored tablets as dosage form." European J. of Pharmaceutical Sciences 21 (2004):305-308. Rodenhuis, et al., attributed the new policy to reports of "bad functioning score lines," "tablets difficult to break," and "unsatisfactory mass uniformity of the subdivided halves." Rodenhuis, et al. noted that "[i]mproving the functioning of score lines may be a more practical approach than banning this [scored] dosage form".

A second problem arising from dividing or breaking of tablets relates to combination drug products, i.e., single or unitary dosage forms containing two or more active ingredients. Combination dosage forms are typically produced as homogeneous mixtures or as capsules. A physician prescribing these homogeneously mixed combination products is unable to adjust the dose of only one of the active ingredients without a proportional adjustment to the dose of the other active ingredient(s). Even if the actives are layered separately, the layer configuration of currently available combination dosage forms results in dividing all layers, thus dividing all active ingredients proportionally. Combination dosage forms can thus be disadvantageous due to the inflexibility for dose adjustment. This disadvantage has hindered the acceptability of certain combination products. Nevertheless, combination treatments for hypertension have proven popular for cost and potential compliance reasons.

Combination products having at least two layers comprising active drug, and a third inactive layer are known. However, these dosage forms comprise the inactive layer interposed as a separating layer between the actives and only serve as a barrier between physical or chemical incompatible active drug-containing layers. The barrier layer does not serve as a means to enable a method of providing a partial dose of the drug or drugs in the combination product.

U.S. Pat. No. 5,738,874 to Conte, et al. describes a multilayer controlled release tablet having a first layer comprising an immediate release drug composition, a second layer comprising a slow release drug composition, and a third layer comprising a barrier composition to modify release of drug from the adjacent layer. This third, drug-free layer is not interposed between the drug-containing layers and is not useful for facilitating breakage or splitting of the tablet to provide accurately divided doses.

US Patent Application, Pub. No. 2005/0019407A1 describes a composite dosage form having first and second portions joined at an interface. These dosage forms have a first molded material and a second compressed material. No disclosure is provided to teach or suggest modifying the dosage forms to facilitate the breaking or subdividing the dosage forms or providing a partial dose.

U.S. Pat. No. 6,602,521 describes a multiplex drug delivery system containing at least two immediate release drug dosage packages enveloped by a scored, extended release compartment. There is no teaching from the disclosure of this patent of a controlled release compartment which does not envelop the immediate release compartments.

Accordingly, there is a need for combination products which can provide the flexibility of adjusting the dose of one of the actives without necessarily adjusting the dose of the other active(s) contained within the combination dosage form.

The present invention, as disclosed herein, can overcome or alleviate the problems discussed above, and can provide additional advantages and address other problems as would be well understood and recognized from this disclosure by persons of ordinary skill in this art.

SUMMARY OF THE INVENTION

The invention provides a method of administering a partial dose of a drug contained in a novel pharmaceutical tablet, said method comprising breaking a pharmaceutical tablet which comprises at least two segments. The method of administering a partial dose of a drug contained in a pharmaceutical tablet of the invention includes breaking the tablet to yield a tablette having a predetermined dose of drug. The tablet is configured as:

1) pharmaceutical tablet that has two or more segments, has a top and a bottom, and has a height that exceeds the width of said tablet, said height being measured vertically from the top to the bottom of said tablet while it is in the tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides;

2) a pharmaceutical tablet having
   (a) a score in a side wherein said score is not oriented vertically and is preferably oriented horizontally; (vertical and horizontal orientation may be determined according to the present disclosure)
   (b) indicia on at least a side that locates a desired breaking region of said tablet;
   (c) a band which is located on one segment or at an interface of two segments; or
   (d) a core of said tablet in which a first lower and a second upper segment have the same color and contain either the same drug in a pharmacologically effective quantity or both lack a pharmacologically effective quantity of any drug, and a third inner, interposed segment that has a different color from said first segment and has either the same drug as said first segment when said first segment has a pharmacologically effective quantity of a drug or has no pharmacologically effective quantity of a drug when said first segment lacks a pharmacologically effective quantity of any drug; or 3) a pharmaceutical tablet having
   (a) two or more segments and each segment either contains the same drug, or the drug in the first and third segments can consist essentially of the same drug or two or more drugs at substantially the same ratio; or else said segment lacks any pharmacologically effective dose of a drug or combination of drugs; or
   (b) said tablet includes a first segment containing a drug or drugs; a third segment containing a drug or drugs which are different from the drug or drugs in said first segment and said first and third segments are physically and chemically compatible; and a second segment that is interposed between said first and third segments and that has an undetectable amount of, or else a pharmacologically ineffective amount of, any drug present in said tablet; or
   (c) said tablet includes a first segment containing a drug or drugs, a third segment containing a drug or drugs which are different from the drug or drugs in said first segment and wherein components of said first and third segments are physically or chemically incompatible, and a second segment that is interposed between said first and said third segment and that has an undetectable amount of, or a pharmacologically ineffective amount of, any drug present in said tablet; said third segment has a height of at least 1.5 mm.

The subject method comprises breaking said tablet at said score or through a substantially inactive segment to form two or more tablettes and enterally administering at least one of said tablettes to a patient.

The core tablets which are preferably adapted for use in the invention are compressed tablets having at least two compositionally distinct segments, with a first segment containing an active drug and a second segment that:

(a) contains the same drug at a lower concentration than the concentration of said drug in said first segment, concentration being dependent on weight/weight ratios of active drug or drugs to excipients within a segment; or
(b) has no detectable drug or the same drug which is in said first segment in a pharmacologically ineffective amount, and said tablet also includes a third segment having the same drug that is present in said first segment; or
(c) has a combination of said drug that is present in said first segment with another drug or drugs not present in a pharmacologically effective quantity or not detectable in said first segment; or
(d) has no detectable drug or the same drug which is in said first segment in a pharmacologically ineffective amount, and said tablet also includes a third segment having a different drug from the drug that is present in said first segment wherein the components of said third segment are compatible with the components of said first segment; or
(e) has no detectable drug or the same drug which is in said first segment in a pharmacologically ineffective amount, and said tablet also includes a third segment having a different drug from the drug that is present in said first segment, said second segment having a vertical height of at least 3 mm and in a preferred embodiment, said second segment has a height greater than the combined height of said first segment and said third segment;
(f) has a different drug than the drug in said first segment and said tablet also includes a third segment having the same drug that is present in said first segment.

The method of administering a partial dose of a drug contained in a pharmaceutical tablet of the invention can include a second segment comprising a color or an absence of color to visually distinguish said second segment from another segment(s). In addition, it would be understood that the descriptions of the three segments in a tablet of the invention can be three segments which form the core structure of a larger tablet.

The invention involves the administration of a part of a pharmaceutical tablet. The terms "active agent," "active drug," "drug," "active pharmaceutical ingredient" and "pharmacologically active agent" may be used interchangeably herein to refer to a chemical material or compound which, when administered to an organism (human or animal) induces a pharmacologic effect, and which includes prescription and non-prescription pharmaceutical compounds, and such substances as pharmacologically effective doses of vitamins or co-factors and the like.

Tablets adapted to be used in the practice of the invention belong to the class of pharmaceutical tablets formulated with two or more layers, and are thus non-homogeneous as a whole, though the active drug or drugs in a particular layer may homogeneously dispersed, or inter-mixed, with excipients within that layer. Tablets of the invention are adapted to be useful not only as whole tablets but also to be breakable into subunits, referred to herein as tablettes, with accurate dosing both as whole tablets and in tablette form. The invention achieves these ends by utilizing in certain of its preferred embodiments a segment that is created from a granulation free of active drug (an "inactive granulation"). The method of administering a partial dose of a drug contained in a pharmaceutical tablet of the subject invention includes dividing a tablet wherein the concentration of the drug, or the quantity of drug, or the amount or ratio of drug contained in the first and third segments is substantially the same.

A primary object of the invention is to provide a method for administering a partial dose of a drug or drugs contained in a whole pharmaceutical tablet adapted to be broken to create a lower dosage (including a dosage of zero) of a drug or drugs present in the whole tablet. The method of the subject invention employs providing a tablet configured to allow breaking through a segment containing no drug, or a minimal concentration of drug or mixture of drugs (on a w/w basis), or a pharmacologically ineffective quantity of drug or mixture of drugs. Alternatively, the breaking can be through a segment that contains a concentration of drug or drugs that is more than minimal concentration of a drug, but which is decreased relative to the drug concentration in another segment of the whole tablet, breaking the tablet into a desired number of "tablettes", for administration of said tablette containing a drug or drugs to a patient.

It is also an object of the invention to provide a method for the accurate dosing of a part of a single agent product or a combination product. The drug or drugs in each segment containing a drug or drugs can be physically and chemically compatible with one another.

With regard to combination products, relevant introductory points are: A mixture of drugs within one granulation acts as a single active drug component in a granulation for purposes of the subject invention in that said two or more admixed drugs within a single segment are inseparable one from another. On the other hand, the invention is useful in the case that a given drug, or mixture of drugs, is present in a pharmacologically effective quantity in one segment, and a different drug or different mixture of drugs, is present in another segment.

In a preferred embodiment in which, for example Drug A is present in a therapeutically effective quantity in an upper segment, an inner segment that lacks a pharmacologically effective quantity of any drug is interposed between two outer (i.e., top and bottom) segments, and Drug B is present in a therapeutically effective quantity in a lower segment, then the method of the invention is most useful in the situation that the height and especially the "effective height" of said inner segment is great enough to allow said inner segment to serve as the breaking region of said tablet substantially without breaking through either outer (top or bottom) segment.

The prior art does not disclose that a "separating" layer or segment has been utilized in an immediate release tablet wherein all ingredients of the upper and lower segments are physically and chemically compatible with each other. In the specialized situation in which active drug or other ingredients of said outer segments are chemically or physically incompatible, the prior art describes any "separating" segment as being limited in height to the minimum needed to substantially diminish or eliminate the incompatibilities in order to minimize the size of the tablet as a whole. A tablet having separate layers forming at least three segments, two of the segments of which contain incompatible compositions, those segments being separated by an excess of an inner segment that allows the inner separating segment to be broken through while retaining the integrity of the outer segments, is novel.

DETAILED DESCRIPTION OF THE INVENTION

Figure 1B:
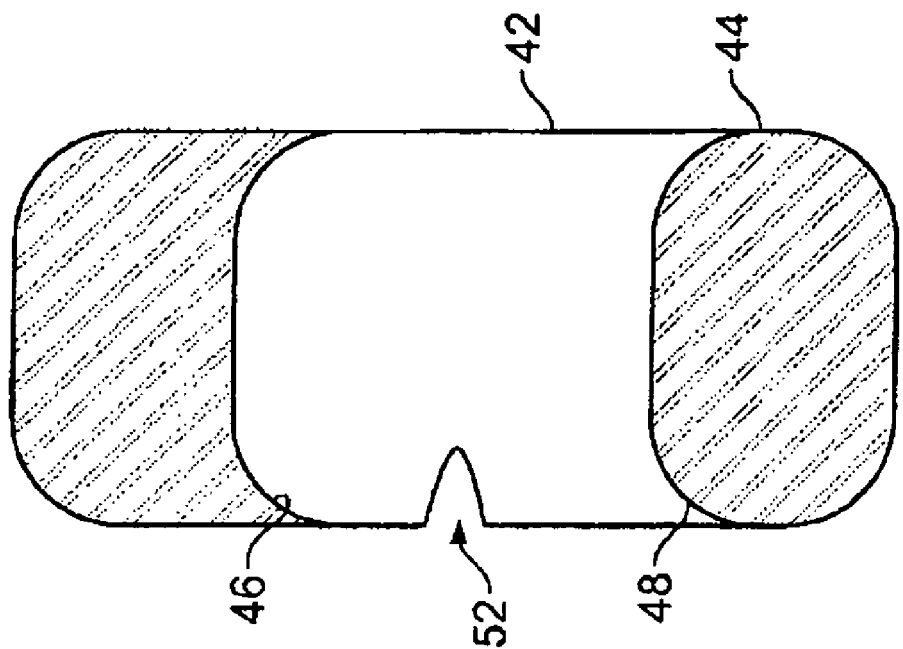
FIG. 1b shows is a cross-section of the tablet of FIG. 1a as viewed from the side of the tablet where the score ends.

Tablets adapted for use in the practice of the invention are preferably produced on a layer press, such as a tri-layer or five-layer high speed press manufactured by Korsch AG of Germany and is commercially available.

The tablets are formed from at least two different granulations; more preferred tablets comprise three vertically disposed segments.

Of the many embodiments of tablets that can be produced for use in the invention, some examples are:

A first granulation comprising amlodipine besylate (or, "amlodipine") enters into a die at a first filling station; a second granulation comprising inactive excipients enters on top of said first granulation at a second filling station; a granulation substantially identical in composition and quantity (weight) to said first granulation enters at a third filling station. After final compression, said tablet is ejected from the die. Each granulation, upon full entry into the die and thereafter, forms a layer. Ideally there is minimal, inadvertent mixing between different granulations in the formation of layers, but some mixing is to be expected and does not alter the improvement in the art of creating breakable tablets from the invention. Different granulations may be of the same or different colors.

By convention herein, the term "segments" may be used in place of "layers" in discussing, generally, the finished tablets of the invention, as explained below.

A segment represents the entirety of a substantially homogeneous contiguous part of a tablet. A segment may be formed from more than one layer, however: If two substantially identical granulations entered the tablet die successively, with the second entering directly after and onto the first, such as at two successive filling stations during automated high-speed tablet manufacture, then the two granulations would each form a separate layer after filling of both is completed, but comprise one segment when compressed. A segment therefore is a basic unit of how the tablets of the invention prove useful. If, however, two different granulations, active drugs, or different salts of the same active drug, were compressed one on top of the other, they would form two segments. Granulations comprising the same active drug but with dissimilar excipients would also form two segments if one granulation were compressed onto another.

A segment formed by a plurality of layers that are formed from substantially identical granulations is called a compound segment. Compound segments may be advantageous in situations of relatively large quantities of an inactive granulation, or granulation containing a drug or drugs, so that two consecutive fills ("feeds") of substantially identical granulations occur.

A more common situation in manufacturing tablets adapted for use in the methods of the subject invention involves a layer formed from a granulation that does not adjoin, and is not contiguous with, a substantially identical granulation. In this case, a simple segment is formed. In other words, a non-compound segment is a simple segment.

As used herein, such terms as "horizontal" ("transverse") and "vertical" when used in relation to a tablet, are based on the spatial orientation of the tablet as, and after, it is produced in a die, but before removal or ejection from the die. Current methods of manufacture produce tablets with one granulation entering the die on top of another, so that tablets of the invention produced in such a manner comprise one or more top (outer) segments, one or more bottom (outer) segments, and optionally one or more middle (inner) segments. A segment that is not a top or bottom (i.e., outer) segment is considered to be an inner segment. The lateral parts of an inner segment have an external surface.

If separate granulations were to be sequentially placed in a die horizontally (side-to-side) and not vertically as is currently the practice, then the tablets so produced would be useful in the present invention as the same product would be produced. When the tablet of FIG. 1, for example, is laid on a flat table, it will tend to lie lengthwise at right angles to the manner in which it is formed in the die, so that if the three segments were all different colors, then the segments would appear to be arranged not vertically (one on top of the other), but rather horizontally (side-to-side). For consistency of terminology, such segments nonetheless are considered herein to be disposed vertically on top of each other.

Tablets adapted for use in the invention are not formed using a cement, glue, adhesive, or the like, and are preferably uncoated.

The term "relatively inactive segment" refers to a segment that either contains an undetectable amount of any drug or contains a decreased concentration of any drug or drugs contained in another segment or segments in a pharmacologically effective quantity. "Decreased concentration" means that the concentration of a drug or drugs in said relatively inactive segment is no more than 80% that of said drug or drugs in another segment, more preferably no more than 20% of said other segment's drug or drugs concentration; most preferably said ratio is no more than 5%, however. The concentration of a drug or drugs in a segment means, herein, the ratio, on a weight to weight basis, of the drug or drugs in said segment to the total weight of said segment.

The tablets adapted for use in the invention are best broken transversely in order to realize their benefits. They may be broken in standard ways such as either by applying force such as a cutting edge directly to the separation mark desired breaking region, or to other areas of the tablet, such as the outer segments, to cause the tablet to break at the desired location.

The drawings depict vertical cross-sectional views of tablets and tablettes for use in the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die as part of the tablet of which they were once parts.

Separation marks are intended to guide tablet breaking in the usual manner that is well known with scores, so that force will be applied to break the tablet at or about the separation mark in a direction that is substantially perpendicular to the surface on which it is desired that breakage of the tablet will be initiated. The tablet may be broken either by applying force such as a cutting edge directly to the separation mark, or to other areas of the tablet, such as the outer segments, to cause the tablet to break at or about the separation mark and in the direction of the separation mark.

The separation mark or marks may comprise one or more of the following:
 (a) a score in a side wherein said score is not oriented vertically;
 (b) indicia on at least side that locates a desired breaking region of said tablet;
 (c) a band which is located on one segment or at an interface of two segments; or
 (d) a core of said tablet in which a first lower and a second upper segment have the same color and contain either the same drug in a pharmacologically effective quantity or both lack a pharmacologically effective quantity of any drug, and a third inner, interposed segment that has a different color from said first segment and has either the same drug as said first segment when said first segment has a pharmacologically effective quantity of a drug or has no pharmacologically effective quantity of a drug when said first segment lacks a pharmacologically effective quantity of any drug.

Figure 2C:
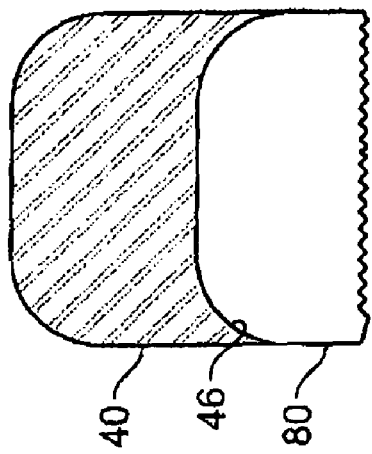
FIGS. 2a-b and 2c-d are views of the tablets shown in FIG. 1a and FIG. 1b, respectively, when the tablets have been broken through the score to form tablettes.
Figure 2D:
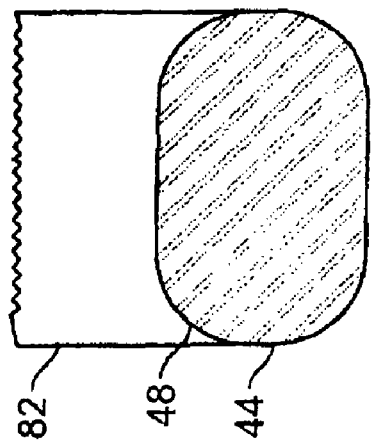
Figure 2A:
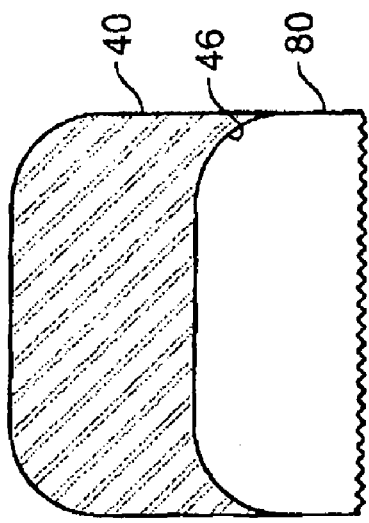
Figure 2B:
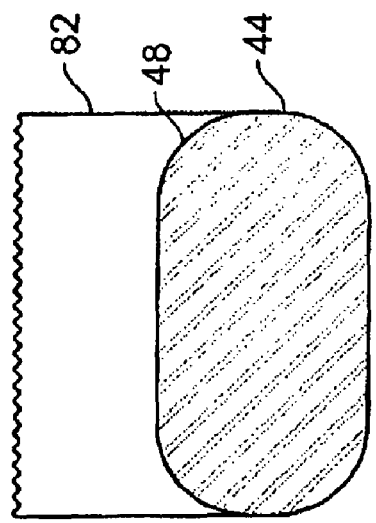

"Front views" refer to a cross-sectional view of a tablet that has a theoretical geometric plane passed through the tablet relative to a side which is arbitrarily designated as the front. Figures labeled as "side view", which also have a corresponding "front view," are taken as a cross-section through the whole tablet from the right side of a front view i.e. a side view is a cross-section that is taken by passing a plane through the vertical axis of the whole tablet at a 90° angle to the cross-sectional front view. Each front view represents a schematic cross-section that passes through the midpoint of the horizontal cross-section as measured from the front of the tablet to the back of the tablet or tablette. The front view is also parallel to the major axis of the tablet (e.g, for a tablet with a rectangular (but not square) transverse cross-section, the longer side of the perimeter is parallel with the plane that depicts the cross-sectional, front view). That plane is located half-way between the front and back surfaces of said tablet. The side views of FIGS. 1b and 2c-d are taken from a vertically-oriented plane that passes through the midpoint of the longer transverse dimension (i.e., the width), and thus are located at and perpendicular to the mid-point of the front view. Drawings are of tablets that have a rectangular but not square horizontal cross-section at the vertical mid-point of the tablet. Segments containing pharmacologically active amounts of a drug or drugs are shown crosshatched; pharmacologically ineffective segments are shown plain (clear, without crosshatching or stippling). The upper part of each figure corresponds to the upper part of a tablet, all of which are depicted as they are situated within a die after final compression and before ejection from the die. For consistency, tablettes are depicted in the same orientation as the tablets from which they are formed, although tablettes are created after tablet ejection from the die. Dotted lines in the tablets depicted in the figures may represent printed marks or other indicia, or scores that are present on or in the surface of the tablet and, if they represent a score, said score does not extend deeply enough into the tablet to appear in the cross-sectional front view. The transverse dotted lines reflecting scores shown in the Figures imply no intention to limit the depth of any scores of the tablets of the invention. Horizontal dotted lines on the front views that represent the surface scores are schematic, and do not necessarily represent the full vertical extent of a score, printed mark, or the like.

Tablettes are depicted with broken surfaces as indicated by a fine saw-tooth pattern. Such saw-tooth depiction is schematic and not intended to represent the actual pattern of breaking of a tablet (or tablette), which often leads to irregular edges even if said tablet is broken through a score.

Separation marks in the tablets depicted in the Figures are depicted as scores that are present on or in the surface of the tablet and that do not extend deeply enough into the tablet to appear in the cross-sectional front views are depicted in the drawings as dotted lines to reflect the location of said scores on or in the surface of the tablet (not shown). It is to be understood that the depth of a separation mark or other score may be deeper than one-half the widest cross-section of the tablet in a particular embodiment, and thus the transverse dotted lines reflecting scores that are separation marks shown in the Figures imply no intention to limit the depth of any scores of the tablets adapted for use in the invention.

Similarly, the tablets shown that contain scores do not limit the width or extent of said scores. The horizontal dotted lines on the front views that represent the surface scores are schematic, and do not necessarily represent the full vertical extent of the score. (Perforations or discontinuous scores through the width or depth of the tablets are not depicted herein, but remain within the scope of the invention, as are other marks on or physical changes to the tablet that create a separation mark.) Any scores or printed indicia that serve as separation marks are for convenience herein assumed to be on the front surface of the tablet, which is arbitrarily chosen from a vertically-oriented surface of the tablets. The "side view" of a tablet is a cross-sectional view of the tablet rotated 90 degrees from the front view, and is shown in FIGS. 2c and 2d. No dimension of the separation marks is limited by their depiction as dotted lines in any figure. Tablettes are depicted with broken surfaces as indicated by a fine saw-tooth pattern. Such saw-tooth depiction is schematic and not intended to represent the actual pattern of breaking of a tablet or tablette.

Figure 1A:
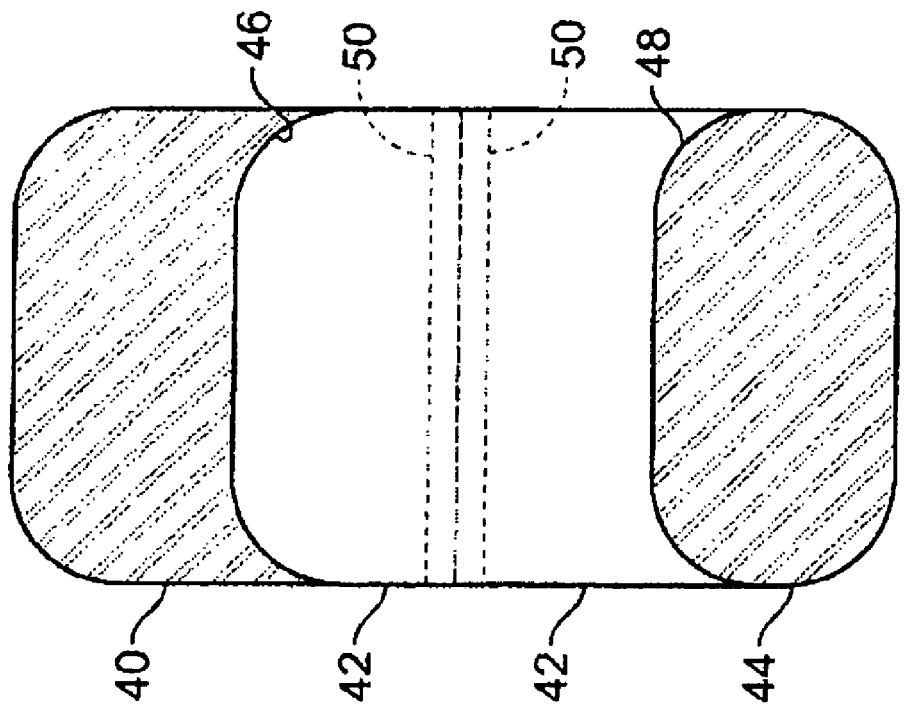
FIG. 1a is shows a cross-section of a taller than wide tablet embodiment of the subject invention, as viewed from the side of the tablet having a score.

FIGS. 1a and 1b depict a tablet with compositionally substantially identical upper segment 40 and lower segment 44. Inner segment 42 contains trace amounts of the drug that is present in a therapeutically effective quantity in each of segments 40 and 44. Interfaces 46 and 48 represent regions in which the upper part of segment 42 and the lower part of segment 42 respectively adjoin upper segment 40 and lower segment 44. The curved interfaces result from the profile of the upper tablet punch which is curved. Score 52 is depicted in FIG. 1b. Dotted line 50 in FIG. 1a is a reflection of score 52 on the surface of the tablet (not shown), that does not penetrate half-way through the shorter transverse axis of the tablet.

FIGS. 2a-d depict tablettes formed from breaking the tablet of FIGS. 1a and 1b through score 52. Inner segment 42 of FIG. 1a no longer exists as an intact segment. The upper tablette of FIGS. 2a and 2c contains segment 80 that adjoins an intact upper segment 40 and the lower tablette contains segment 82 and intact segment 44.

Breaking the tablet of FIGS. 1a and 1b through the score placed in segment 42 is clearly easier than breaking the tablet through its vertical dimension, which is currently the practice with scored layered (segmented) tablets. The fact that no break is made in the parts of the tablet where the active drug has been place provides for exceptionally accurate breaking relative to the active drug or drugs contained in the tablet.

Figure 3:
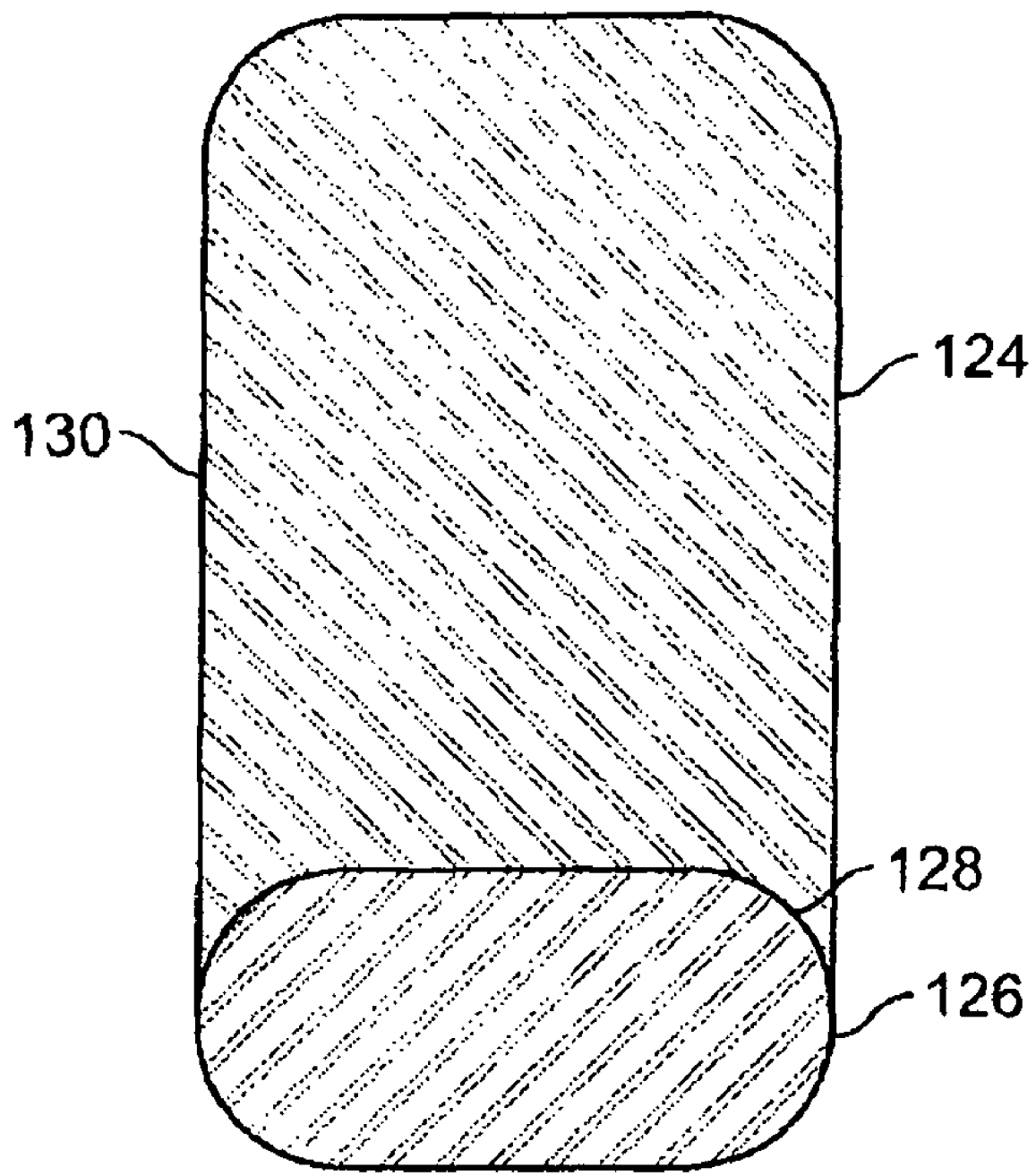
FIG. 3 is shows a cross-section of a taller than wide tablet, illustrating an embodiment of the subject invention having two segments, one of which is about three-quarters of the length of the tablet.

FIG. 3 shows a two-segment tablet, each segment formed from a granulation containing a pharmacologically effective amount of medication. Upper (outer) segment 124 is larger than lower (outer) segment 126. Interface 128 indicates a region at which said segments are contiguous. A printed mark on the outer surface of the tablet (not shown) indicates a desired breaking point, as indicated by the location of arrow 130 that reflects the position of said surface printed mark. The two segments also have different colors, however, further allowing identification of which part of the tablet contains which segment.

Figure 4A:
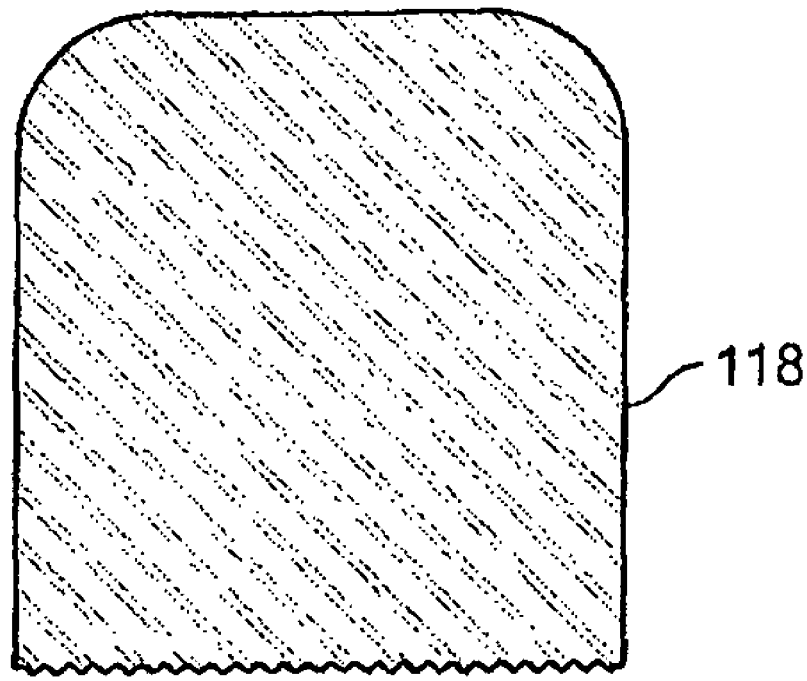
FIGS. 4a-4b are views show a tablet of FIG. 3 when the tablet has been broken at the approximate mid-point of the tablet.
Figure 4B:
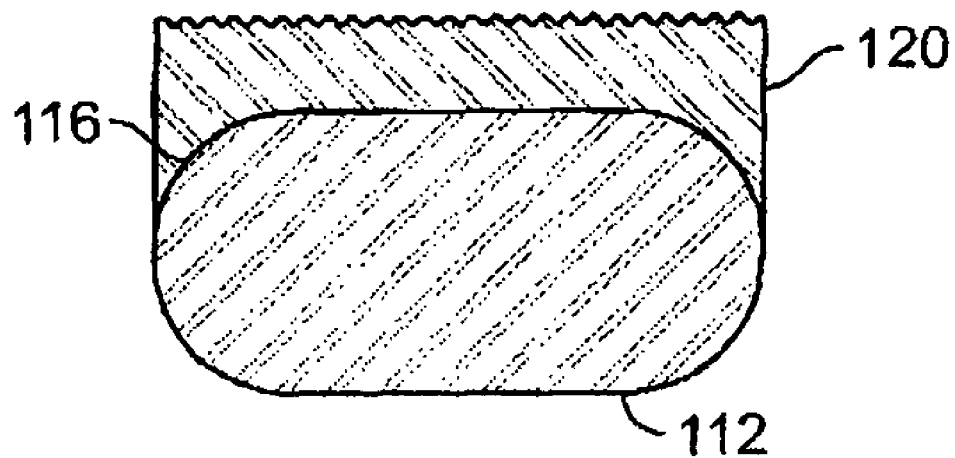

FIGS. 4a and 4b depict the two tablettes formed by breaking the tablet of FIG. 3. The tablette of FIG. 4a consists of segment 118, which represents the bulk of segment 124 of FIG. 3. The tablette depicted in FIG. 4b contains segment 112 in an intact form and segment 120, which represents a less than half-portion of segment 124 of FIG. 3. Interface 116 indicates a region at which said segments are contiguous. The curved face is due to the profile of the tablet punch.

Figure 5:
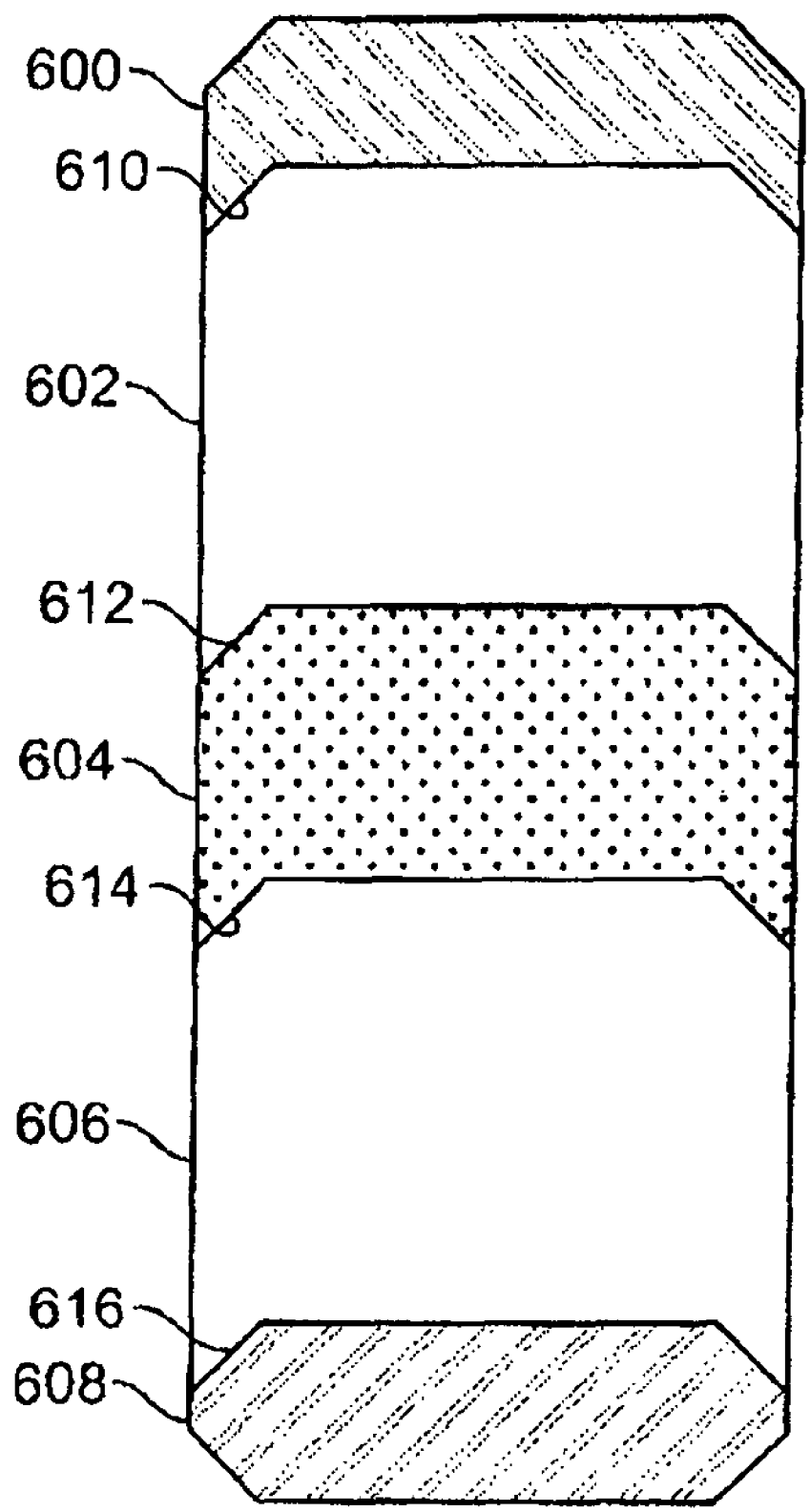
FIG. 5 shows is a cross-section of a taller than wide tablet, illustrating an embodiment having five layered segments.

FIG. 5 illustrates a tablet more elongated than those previously demonstrated. This tablet is adapted, even more than the others, for ease of breaking through one segment. Upper segment 600 is provided with a therapeutic quantity of a drug; stippled inner segment 604 is provided with a therapeutic quantity of a different drug; and, lower segment 608 is provided with a therapeutic quantity of a drug different from that found in a therapeutic quantity in segments 600 and 604. Clear (plain) inner segments 602 and 606 contain pharmacologically ineffective amounts of each of the three drugs found in the tablet. Interfaces 610, 612, 614, and 616 represent the regions at which two contiguous segments adjoin. The tablet of FIG. 5 is provided with a different color for each segment. Even though there is no surface scoring or indicia, the color scheme is such that a person's attention may be directed to apply force to break the tablet through segment 602 to create the tablettes depicted in FIGS. 6a and 6b.

Figure 6A:
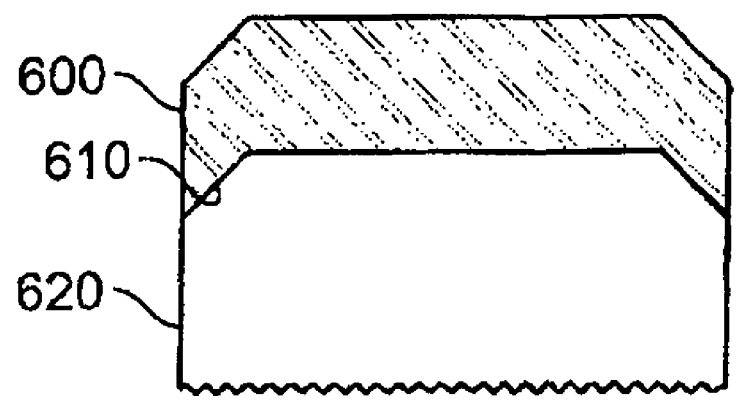
FIGS. 6a-b are views of a five-segment tablet of FIG. 5 when the tablet has been broken through one segment to form tablettes.
Figure 6B:
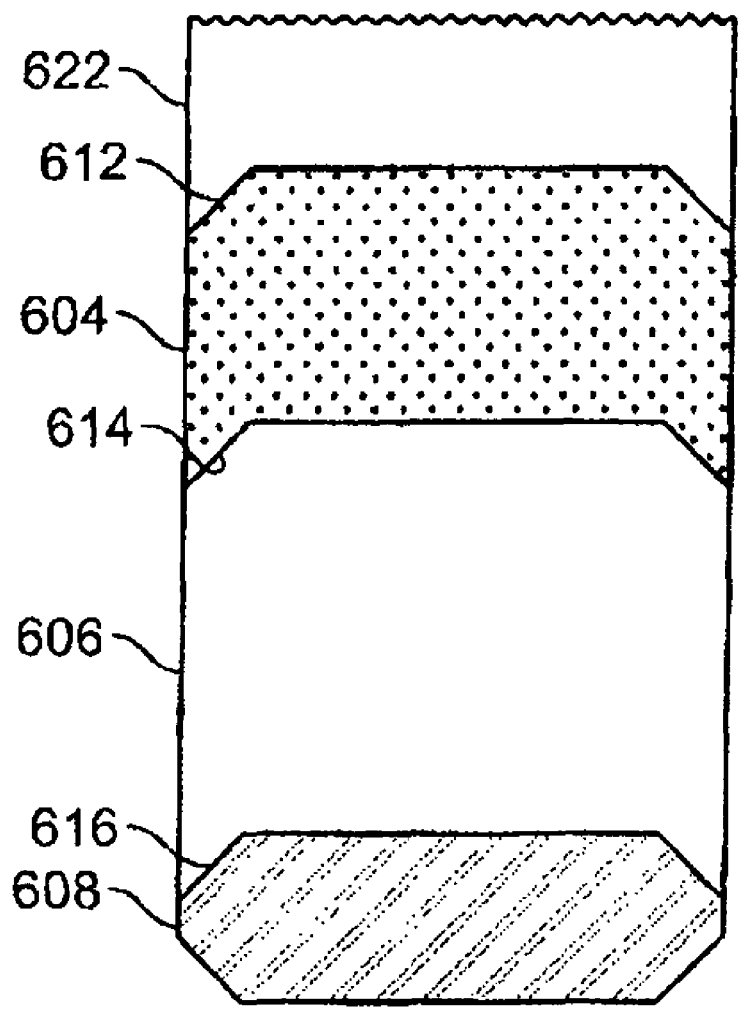

FIG. 6a depicts the smaller tablette created by breaking the tablet of FIG. 5 through segment 602 in a transverse fashion. Segment 620 has been created by said breaking, and segment 602 of FIG. 5 no longer exists as a intact segment. FIG. 6b depicts the larger tablette created by said breaking of the tablet of FIG. 5. New upper segment 622 has been created.

Figure 7A:
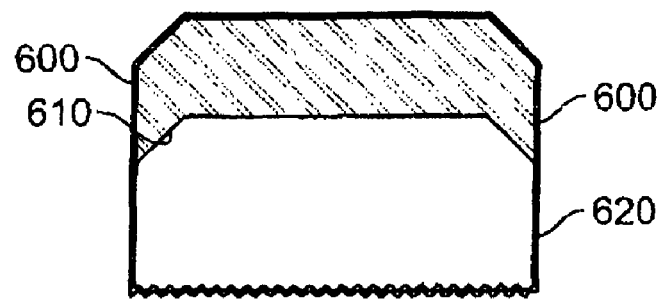
FIGS. 7a-c are views of a tablet of FIG. 5 when the tablet has effectively been broken through two segments in two steps, first by breaking the tablet into tablettes and then by breaking the tablette of FIG. 6b.
Figure 7B:
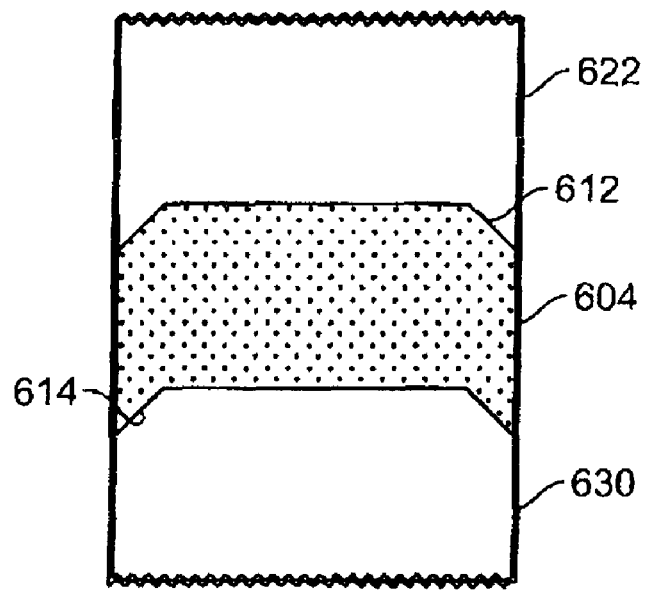
Figure 7C:
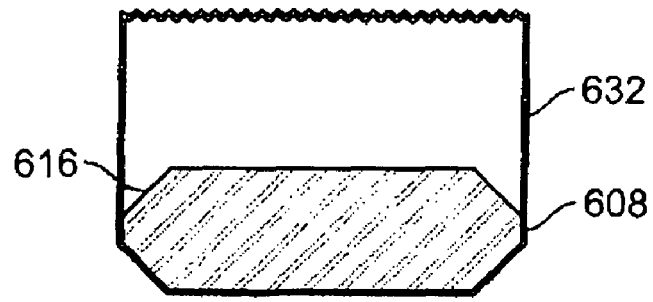

FIGS. 7a-7c depict three tablettes created by the subsequent breaking of the tablette of FIG. 6b. New segment 630 and segment 632 have been created and segment 606 no longer exists as an intact segment.

Figure 8:
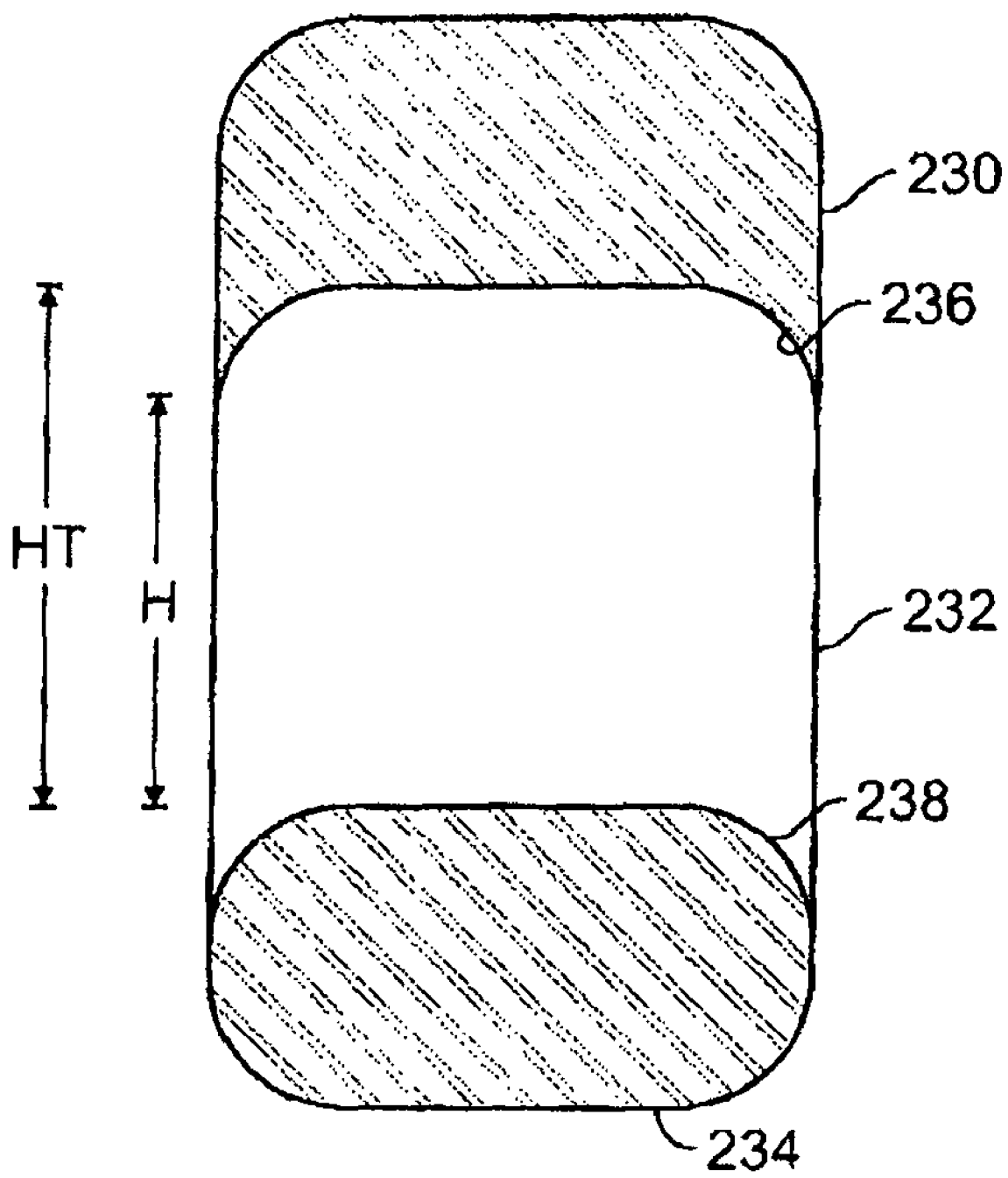
FIG. 8 is a cross-section of a tablet having three segments.

FIG. 8 is a cross-section of a three segment tablet, having a top segment 230 having a drug, an inactive middle segment (no detectable drug or a pharmacologically ineffective amount of a drug) and a bottom segment which contains the same drug as the top segment. This tablet is formed with a tablet punch having a curved profile which forms curved interfaces 236 and 238 as well as the top of the tablet. The effective height of the middle segment is H which is less than the actual height HT of the middle segment due to the effect of the curved tablet punch. It is desired to break this type of a tablet only through that part of the middle segment within the effective height H to avoid breaking into the drug containing top or bottom segment.

The above-described tablet contains three layers, and three segments may contain amlodipine. It may be broken through the segment formed from the inactive granulation. Said breaking, if confined solely to said middle granulation, will create two tablettes, each containing one substantially intact segment comprising amlodipine and a part of the middle segment. The advance in the art of tablet splitting is that maximal accuracy of the dose in each tablette will be achieved, since any weight (or, mass) difference between the two tablettes will be due to differences in the quantity of middle segment present, but said middle segment is expected to have little if any amlodipine therein. Similarly, any loss of mass due to chipping or crumbling is expected to occur in the middle segment.

Figure 9:
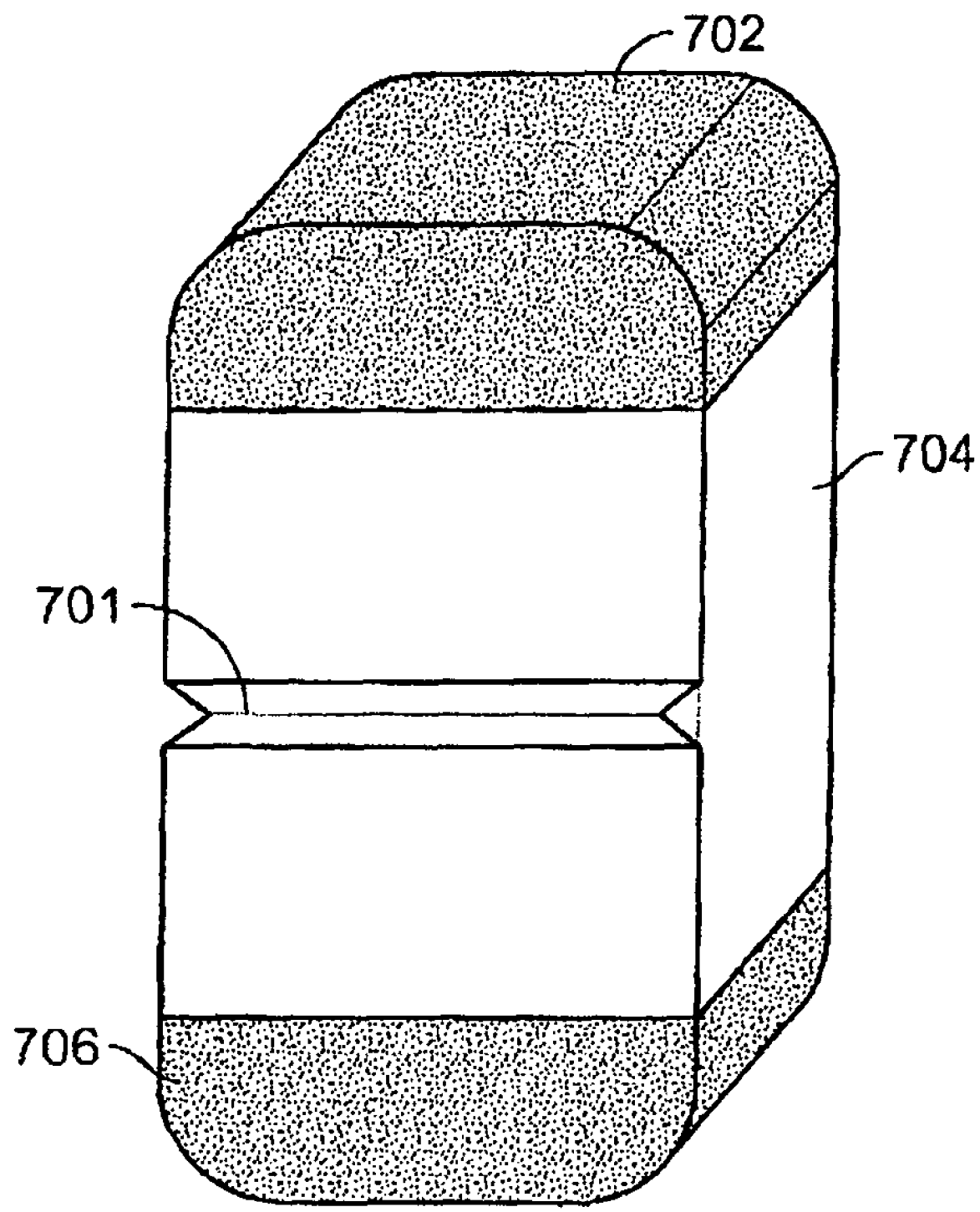
FIG. 9 is a perspective view of a scored tablet according to the invention.

FIG. 9 is a perspective view of a tablet adapted for use in the invention which shows score 701 as a separating mark on a front surface and top active (drug containing) segment 702; middle inactive segment (no detectable drug or a pharmacologically ineffective amount of a drug) and bottom active segment 706. When the tablet is broken at the score 701, the top segment and the bottom segment will remain intact.

Figure 10:
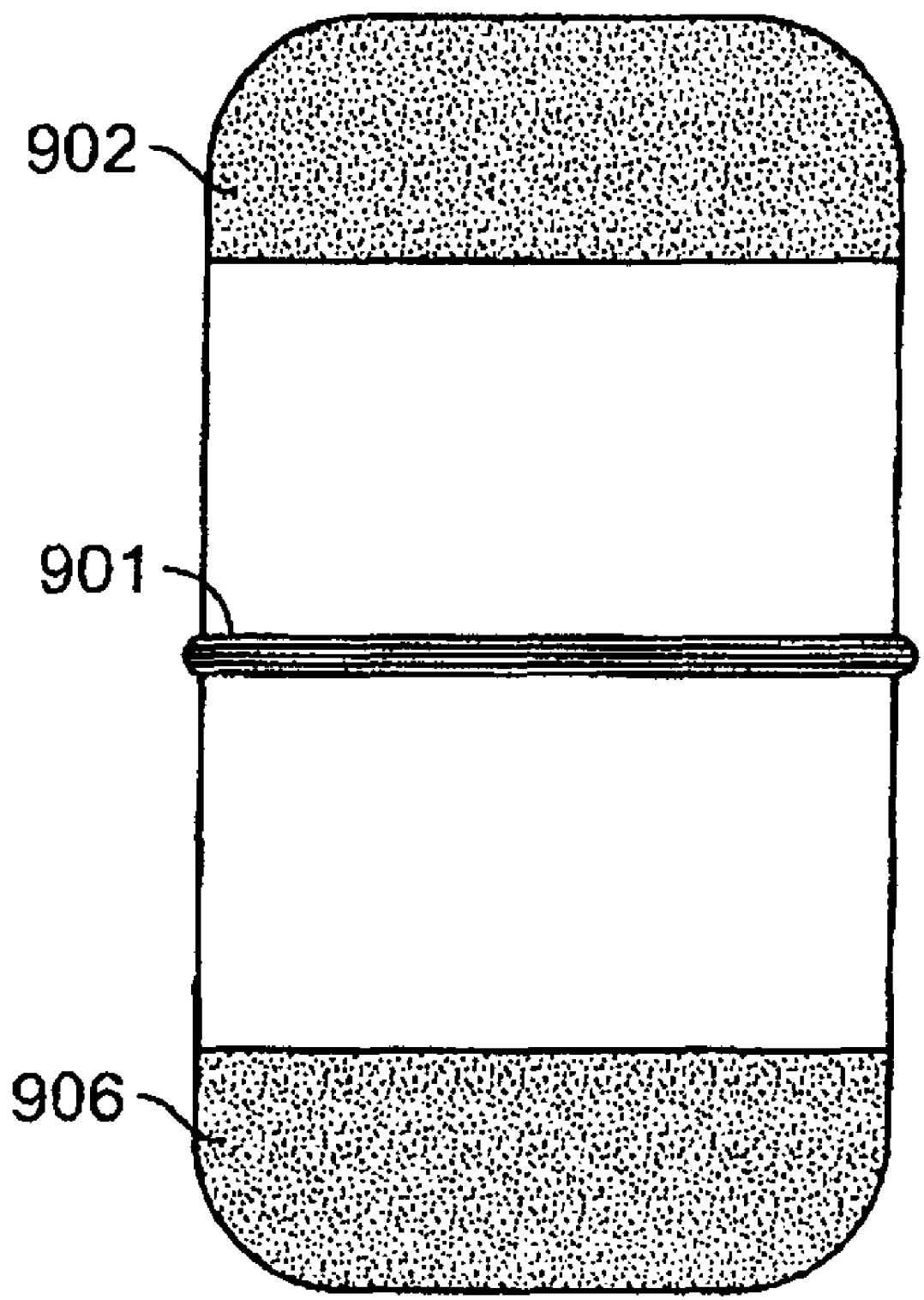
FIG. 10 is a front view of a banded capsule according to the invention.

FIG. 10 is a front view of a tablet adapted for use in the invention showing a band 901, such as a gelatin band that is used to seal hard gelatin capsules, which is applied to suitable tablets according to the invention to provide a separating mark. Techniques such as those used to band capsules, as disclosed in U.S. Pat. No. 4,922,682, which is incorporated by reference, may be modified to provide a band in making tablets according to the invention.

Figure 11:
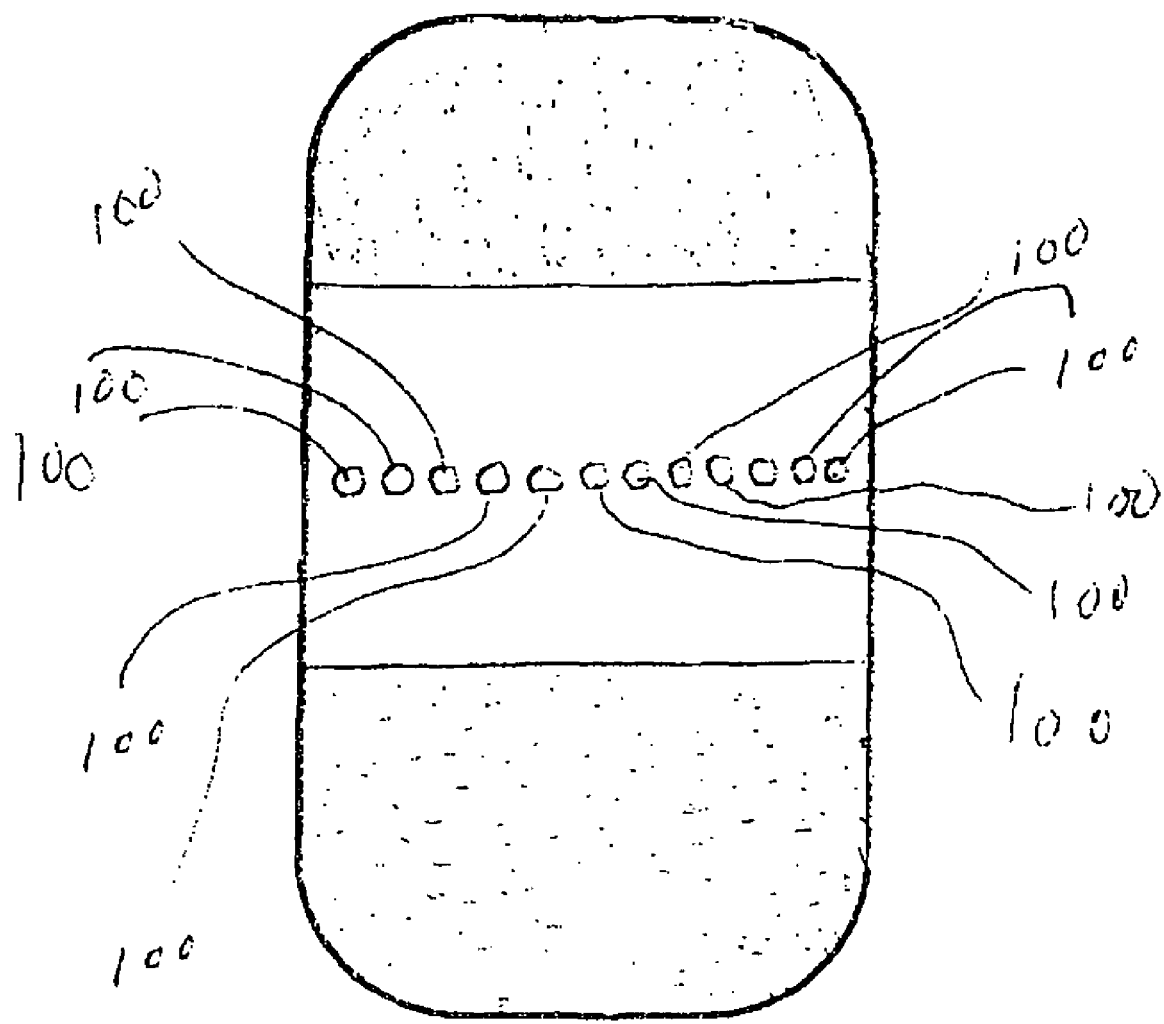
FIG. 11 is a front view of a tablet having perforations in the surface according to the invention.

FIG. 11 shows a series of perforations 100 that may be made in the surface of a tablet to form a separation mark according to the invention. These perforations may be formed e.g. by mechanical or laser drilling 1-2 mm diameter holes that extend into the surface to a depth of 1-2 mm.

Figure 12:
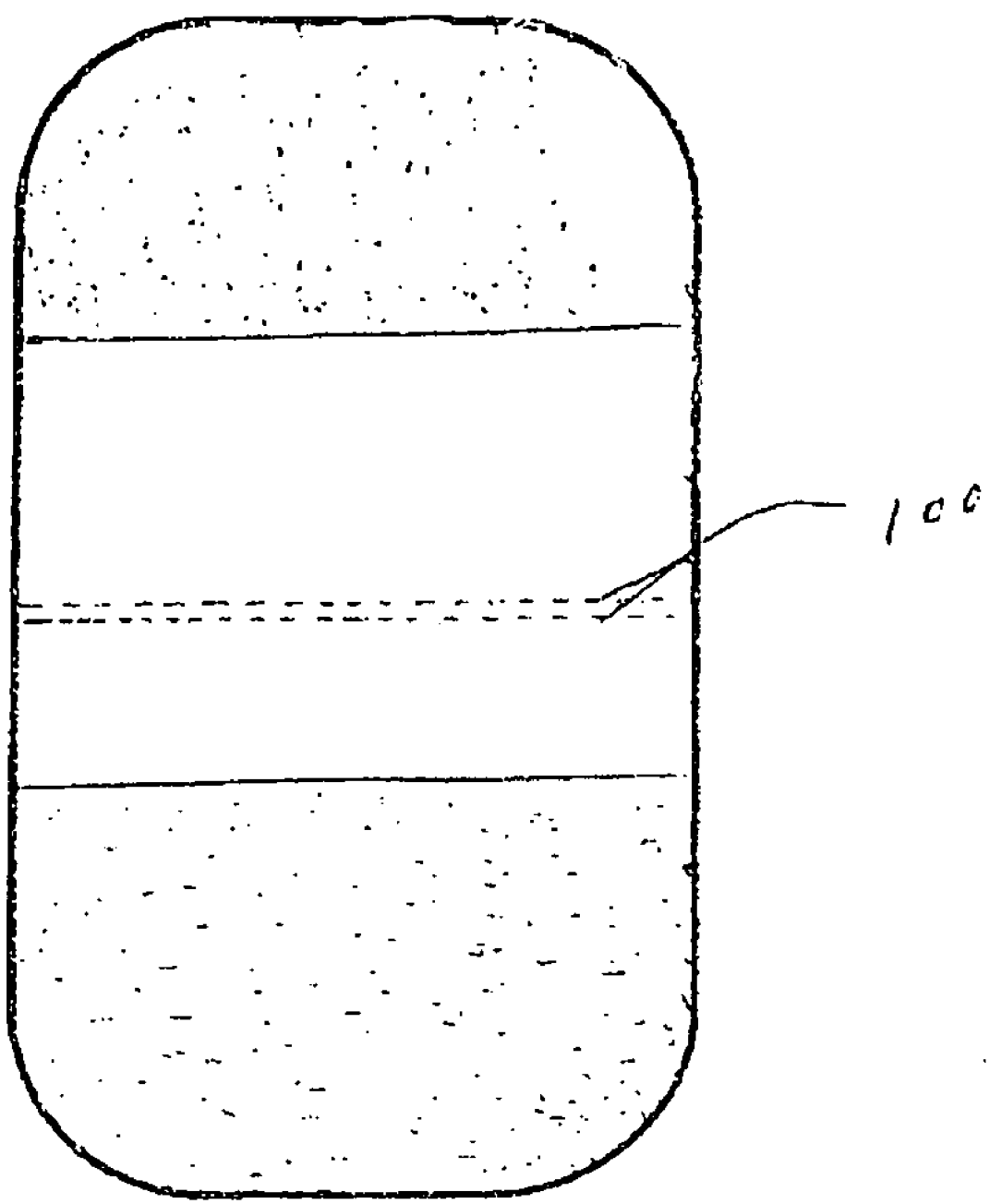
FIG. 12 is a front view of a tablet having two printed dotted lines printed on the surface according to the invention.

FIG. 12 shows a front view of a tablet adapted for use in the invention that has two printed dotted lines that serve as a separation mark.

Another preferred tablet for use in the practice of the invention utilizes a variation on the above, for example:

A first granulation comprising hydrochlorothiazide (HCTZ) enters the die, followed by an inactive granulation entering the die twice, followed at the fourth and final filling station by a granulation comprising bisoprolol (a beta-blocker). After final compression, a tablet consisting of three segments (formed from four layers) has been created. The layer formed from the first granulation is the bottom layer, the layers formed from inactive excipients are the two inner layers and together, after tablet formation, make up the middle (inner) segment, and the final granulation comprises the top layer, which after final compression is denoted the top segment. Thus all dimensions and directions herein relate to the method of manufacture of the tablet. This preferably taller than wider tablet may contain some amount of HCTZ in the middle and top segments, and may contain some amount of bisoprolol in the middle and bottom segments.

After breaking the above tablet entirely through the middle segment, two tablettes are formed. One contains primarily the full, presumably therapeutically effective quantity of HCTZ and probably some amount, preferably trace, of bisoprolol; the other contains primarily the full amount of bisoprolol and probably some amount, preferably trace, of HCTZ, plus some quantity of said middle segment. Important therapeutic benefits in terms of dosage adjustment, side effect management, and the like are obtained from the present invention.

As FIG. 8 demonstrates, cupping or beveling of the upper punch commonly causes the peripheral parts of any segment other than the lowest segment, to extend below the level of the central part of that segment. In order to fully realize the benefit of a "separating segment" per the invention, it is optimal that a transverse plane be able to be placed between the lowest part of a superiorly disposed segment, and the highest part of an inferiorly disposed segment, with said plane passing between an interposed, preferably pharmacologically inactive segment. The vertical distance between the lowest part of a superiorly disposed segment and the highest part of an inferiorly disposed segment is herein denoted the effective height H. Generally, that measurement will be from the vertical height from the bottom of the tablet to the plane drawn horizontally from the periphery of the higher segment, due to the cupping or beveling of such a segment, and from the vertical height from the bottom of the tablet to the center of the lower segment.

The effective height in the case of beveling or cupping of segments, as easily reflected in the shape of the top of the tablet, is always less than the height of the separating or interposed segment through which breaking is intended to occur. The height of an interposed segment is the vertical distance from its highest point to the highest point of the contiguous superiorly disposed segment.

In the case of separating or interposed segments, prior art limits the height to approximately 1 mm for immediate release pharmaceutical tablets. The effective height H has been limited to less than that. Preferred tablets of the invention often use a height and an effective height H that are both over 4 mm, and may exceed 6 mm. Lesser heights and effective heights are utilized when needed due to size constraints on the tablet. The segment derived from the second granulation preferably has an effective height which is at least about 1.5 mm, and can be about 1.5 mm to about 3 mm, or can be greater than 4 mm.

A further benefit of the invention may relate to pediatric or geriatric doses, which may not be produced in appropriate dose strengths. In the case of amlodipine, a 1.25 mg daily dose may be useful in either small children with hypertension, or in frail elderly patients with angina or hypertension, who may have hepatic dysfunction. Even though the United States Food and Drug Administration (FDA) has not approved a 1.25 mg dose, precise divisibility of the approved 2.5 mg dose would allow a 1.25 mg daily dose. In addition, precise divisibility of the approved 2.5 mg dose will allow accurate dosing of 3.75 mg daily.

Another use of the invention is to enable a method of cost savings to insurers and patients. The invention allows this because many drugs, such as Norvasc® and Coumadin®, have pricing that differs little (if at all) between different doses. Because tablet splitting is imprecise for most scored tablets, the practice of mandatory splitting has been met with disapproval by most physician and pharmacist organizations. The invention provides accurate partial dosing of the drug or drugs in a tablet (or some tablettes) according to the invention as described herein. Substantial benefits are foreseen from this innovation. In addition, the ability to separate one active drug from another in a combination product has cost saving advantages, as well.

It is recognized that related inventions may be within the spirit of the disclosures herein. Also, no omission in the current application is intended to limit the inventors to the current claims or disclosures. While certain preferred and alternative embodiments of the invention have been set forth for purposes of disclosing the invention, modifications to the disclosed embodiments may occur to those who are skilled in the art.

The invention claimed is:

1. A method of administering a partial dose of a drug contained in a pharmaceutical tablet, said method comprising:
   (a) providing a tablet comprising at least a first and second segment which are compositionally distinct, said first segment containing a drug in a pharmacologically effective amount and said second segment:
      (i) contains no detectable drug or the same drug which is in said first segment in a pharmacologically ineffective amount and also includes a third segment having the same drug that is present in said first segment; and
      (ii) said second segment is interposed between said first and third segments;
   (b) breaking said tablet through the second segment without damage to the first or third segments to form two or more tablettes; and
   (c) enterally administering to a patient at least one tablette formed by said breaking of the tablet.

2. The method of administering a partial dose of a drug contained in a pharmaceutical tablet as defined in claim 1 wherein said second segment has a height greater than the combined height of said first segment and said third segment.

3. The method of administering a partial dose of a drug contained in a pharmaceutical tablet as defined in claim 1 wherein the concentration of the drug in said first and third segments is substantially the same.

4. The method of administering a partial dose of a drug contained in a pharmaceutical tablet as defined in claim 1 in which the quantity of drug in said first and third segments is substantially the same.

5. The method of administering a partial dose of a drug contained in a pharmaceutical tablet as defined in claim 1 in which said first segment and said third segment are substantially compositionally identical.

6. The method of administering a partial dose of a drug contained in a pharmaceutical tablet as defined in claim 1 in which said first segment and said third segment contain substantially identical quantities of the same drug or drugs, where the amount or ratio of said drug or drugs is the same in both segments.

7. The method of administering a partial dose of a drug contained in a pharmaceutical tablet as defined in claim 1 in which said second segment comprises a color or an absence of color to visually distinguish said second segment from another segment.

8. The method of administering a partial dose of a drug contained in a pharmaceutical tablet as defined in claim 1 in which breaking said tablet, yields a tablette having a predetermined dose of drug.

9. The method of administering a partial dose of a drug contained in a pharmaceutical tablet as defined in claim 1 in which the first segment and third segment consist essentially of the same drug.

10. The method of administering a partial dose of a drug contained in a pharmaceutical tablet as defined in claims 1 in which the second segment corresponds to a segment located in the middle of the tablet.

11. The method of administering a partial dose of a drug contained in a pharmaceutical tablet as defined in claim 1 wherein one or more of said segments comprises at least one separation mark selected from a score, perforation, printed or gelatin mark, or a combination of thereof, placed on or within said one or more segments.

12. The method of claim 11, wherein said score, perforation, printed or gelatin mark, or combination thereof is placed on said second segment interposed between the first and third segments, and is predominantly oriented to guide tablet breaking through said second segment substantially without breaking through said first segment or said third segment.

13. A method of administering a partial dose of a drug contained in a pharmaceutical tablet, said method comprising:
   (a) providing a tablet produced sequentially from a first active granulation comprising a drug or drugs, a second granulation that contains no detectable drug or a pharmacologically inactive amount of a drug or drugs, and a third active granulation comprising a different active drug or drugs than said first granulation, wherein said second segment is interposed between the first and third segments:
      (i) all granulations in the tablet are physically and chemically compatible; or
      (ii) the segment derived from the second granulation has an effective height of at least 1.5 mm,
   (b) breaking said tablet through said second granulation to form two or more tablettes, and
   (c) enterally administering at least one of said tablettes to a patient.

14. The method of administering a partial dose of a drug contained in a pharmaceutical tablet as defined in claim 13 in which said segment derived from the second granulation has an effective height of greater than 4 mm.

15. The method of administering a partial dose of a drug contained in a pharmaceutical tablet as defined in claim 13 in which said segment derived from the second granulation has an effective height of about 1.5 mm to about 3 mm.

16. The method of administering a partial dose of a drug contained in a pharmaceutical tablet as defined in claim 13 in which the tablet consists of three segments.

17. The method of administering a partial dose of a drug contained in a pharmaceutical tablet as defined in claim 13 in which said second granulation has an amount of drug or drugs which is pharmacologically inactive.

18. The method of administering a partial dose of a drug contained in a pharmaceutical tablet as defined in claim 13 in which at least one granulation having no detectable active drug or a pharmacologically inactive amount of an active drug is interposed between said first and third granulations.

19. The method of administering a partial dose of a drug contained in a pharmaceutical tablet as defined in claim 13 in which said first, second and third granulations have a color which allows for the identification of each tablet segment.

20. The method of administering a partial dose of a drug contained in a pharmaceutical tablet as defined in claim 13 in which the second segment comprises a separation mark.

21. The method of claim 20 wherein said separation mark is a score.

22. A method of administering a precise partial dose of a drug in a compressed pharmaceutical tablet to a patient, said method comprising:
   (a) providing a tablet having at least three segments including a first and third active segment and a second inactive segment interposed between the first and third segments, and a top and a bottom and has a height that exceeds the width of said tablet, said height being measured vertically from the top to the bottom of said tablet while it is in the tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides to a patient, (b) breaking said tablet through the second inactive segment without damage to the active segments to create one or more tablette, and (c) administering at least one of said tablettes to said patient.

23. The method of claim 22 wherein said tablet comprises three segments, said three segments comprising a second segment being an inner interposed segment between a first segment and a third segment, said inner interposed segment being substantially inactive or having an amount of a drug or drugs which is pharmacologically ineffective, said first segment being an upper segment, and said third segment being a lower segment, said first and third segments being substantially identical.

24. The method of claim 22, wherein said tablet is a core structure of a larger tablet.

25. The method of claim 22 wherein said tablet comprises a separation mark.

26. The method of claim 22 wherein said segments comprising a drug or drugs contain the same drug or drugs.

27. The method of claim 26 wherein said tablet contains two or more segments that have different concentrations of a drug or drugs, relative to inactive excipients in each segment, on a weight to weight basis.

* * * * *